United States Patent
Fuhrman et al.

(10) Patent No.: US 7,788,113 B2
(45) Date of Patent: Aug. 31, 2010

(54) METHODS FOR DEVELOPING AND CONDUCTING A NUTRITIONAL TREATMENT PROGRAM

(75) Inventors: Joel H. Fuhrman, Flemington, NJ (US); Kevin Leville, New Canaan, CT (US)

(73) Assignee: Nutritional Excellence, LLC, New Canaan, CT (US)

( * ) Notice: Subject to any disclaimer, the term of this patent is extended or adjusted under 35 U.S.C. 154(b) by 181 days.

(21) Appl. No.: 11/936,018

(22) Filed: Nov. 6, 2007

(65) Prior Publication Data

US 2008/0177572 A1 Jul. 24, 2008

Related U.S. Application Data

(63) Continuation-in-part of application No. 11/906,239, filed on Oct. 1, 2007, now abandoned.

(60) Provisional application No. 60/848,499, filed on Sep. 29, 2006.

(51) Int. Cl.
*G06Q 10/00* (2006.01)

(52) U.S. Cl. .................................... 705/2

(58) Field of Classification Search ............... 705/2, 705/3, 4
See application file for complete search history.

(56) References Cited

U.S. PATENT DOCUMENTS 6,953,342 B2 * 10/2005 Bisogno ............... 434/127
7,039,592 B1 * 5/2006 Yegge et al. ............... 705/4

* cited by examiner

*Primary Examiner*—Gerald J. O'Connor
*Assistant Examiner*—Edward Winston
(74) *Attorney, Agent, or Firm*—The Nath Law Group; Laurie A. Axford

(57) ABSTRACT

The present invention relates to methods for developing and conducting a nutritional treatment program. In one embodiment, the present invention relates to methods for developing and conducting a nutritional treatment program to promote weight loss, or to treat or prevent other disease states, such as diabetes, heart disease, hypertension, etc. For example, such methods are employed to develop a diet program, and more particularly to methods for developing a program for both dieting and maintaining good nutrition both before and after losing weight. In another embodiment, the present invention relates to personalized nutritional treatment programs that are computer implemented and dynamic based on a subject's changing health condition.

2 Claims, 4 Drawing Sheets

"ANDI'S" and "MANDI's" of Commonly Eaten Foods

Vegetables

| | ANDI | Serving Size | MANDI |
|---|---|---|---|
| Mustard Greens, cooked | 1000 | 1.5 cups | 25.0 |
| Watercress, raw | 1000 | 3 cups | 17.0 |
| Kale, cooked | 1000 | 1.5 cups | 25.0 |
| Turnip Greens, cooked | 1000 | 1.5 cups | 25.0 |
| Collard Greens, cooked | 1000 | 1.5 cups | 33.0 |
| Bok Choy, cooked | 824 | 1.5 cups | 20.6 |
| Spinach, raw | 739 | 5 cups | 18.5 |
| Spinach, cooked | 697 | 1.5 cups | 23.0 |
| Brussels Sprouts | 672 | 2 cups | 27.6 |
| Swiss Chard, cooked | 670 | 1.5 cups | 16.8 |
| Arugula, raw | 560 | 5 cups | 9.5 |
| Radish | 554 | 6 items | 9.4 |
| Bean Sprouts | 444 | 1 cup | 11.1 |
| Red Pepper | 420 | 1.5 cups | 10.5 |
| Cabbage, raw | 420 | 1.5 cups | 10.5 |
| Romaine | 389 | 5 cups | 9.7 |
| Broccoli, raw | 376 | 1.5 cups | 9.4 |
| Vegetable Juice | 367 | 8 oz | 9.2 |
| Boston Lettuce | 353 | 5 cups | 8.8 |
| Carrot Juice | 344 | 1 cup | 14.1 |
| Broccoli, cooked | 342 | 2 cups | 14.0 |
| Dandelion Greens, cooked | 329 | 1.5 cups | 8.2 |
| Escarole, raw | 322 | 3 cups | 5.5 |
| Cauliflower | 285 | 1.5 cups | 7.4 |
| Green Pepper | 258 | 1.5 cups | 6.5 |
| Tomato Sauce | 248 | ½ cup | 6.2 |
| Artichoke | 244 | 2 items | 12.0 |
| Carrots, raw | 240 | 1.5 cups | 7.9 |
| Salsa | 236 | ¼ cup | 5.9 |
| Asparagus | 234 | 2.0 cups | 7.7 |
| Zucchini | 222 | 2.5 cups (1 item) | 5.6 |
| Tomato, diced | 164 | 2 cups | 5.4 |
| Butternut Squash | 159 | 1.5 cups | 7.8 |
| Celery | 135 | 1.5 cups | 2.3 |
| Mushrooms | 134 | 1.5 cups | 2.3 |
| Iceberg Lettuce | 110 | 5 cups | 2.8 |
| Beets | 97 | 1.5 cups | 4.0 |
| Eggplant | 97 | 2 cups | 3.2 |
| Sweet Potato | 84 | 1 cup | 5.3 |
| Green Peas | 70 | 1.5 cups | 4.1 |
| Cucumber | 50 | 1 item | 1.2 |
| Onions | 47 | 1 cup | 1.2 |
| Potato | 31 | 1.5 cups | 1.7 |
| Corn | 25 | 1.5 cups | 1.6 |

Figure 1
"ANDI'S" and "MANDI's" of Commonly Eaten Foods

Vegetables

| | ANDI | Serving Size | MANDI |
|---|---|---|---|
| Mustard Greens, cooked | 1000 | 1.5 cups | 25.0 |
| Watercress, raw | 1000 | 3 cups | 17.0 |
| Kale, cooked | 1000 | 1.5 cups | 25.0 |
| Turnip Greens, cooked | 1000 | 1.5 cups | 25.0 |
| Collard Greens, cooked | 1000 | 1.5 cups | 33.0 |
| Bok Choy, cooked | 824 | 1.5 cups | 20.6 |
| Spinach, raw | 739 | 5 cups | 18.5 |
| Spinach, cooked | 697 | 1.5 cups | 23.0 |
| Brussels Sprouts | 672 | 2 cups | 27.6 |
| Swiss Chard, cooked | 670 | 1.5 cups | 16.8 |
| Arugula, raw | 560 | 5 cups | 9.5 |
| Radish | 554 | 6 items | 9.4 |
| Bean Sprouts | 444 | 1 cup | 11.1 |
| Red Pepper | 420 | 1.5 cups | 10.5 |
| Cabbage, raw | 420 | 1.5 cups | 10.5 |
| Romaine | 389 | 5 cups | 9.7 |
| Broccoli, raw | 376 | 1.5 cups | 9.4 |
| Vegetable Juice | 367 | 8 oz | 9.2 |
| Boston Lettuce | 353 | 5 cups | 8.8 |
| Carrot Juice | 344 | 1 cup | 14.1 |
| Broccoli, cooked | 342 | 2 cups | 14.0 |
| Dandelion Greens, cooked | 329 | 1.5 cups | 8.2 |
| Escarole, raw | 322 | 3 cups | 5.5 |
| Cauliflower | 285 | 1.5 cups | 7.4 |
| Green Pepper | 258 | 1.5 cups | 6.5 |
| Tomato Sauce | 248 | ½ cup | 6.2 |
| Artichoke | 244 | 2 items | 12.0 |
| Carrots, raw | 240 | 1.5 cups | 7.9 |
| Salsa | 236 | ¼ cup | 5.9 |
| Asparagus | 234 | 2.0 cups | 7.7 |
| Zucchini | 222 | 2.5 cups (1 item) | 5.6 |
| Tomato, diced | 164 | 2 cups | 5.4 |
| Butternut Squash | 159 | 1.5 cups | 7.8 |
| Celery | 135 | 1.5 cups | 2.3 |
| Mushrooms | 134 | 1.5 cups | 2.3 |
| Iceberg Lettuce | 110 | 5 cups | 2.8 |
| Beets | 97 | 1.5 cups | 4.0 |
| Eggplant | 97 | 2 cups | 3.2 |
| Sweet Potato | 84 | 1 cup | 5.3 |
| Green Peas | 70 | 1.5 cups | 4.1 |
| Cucumber | 50 | 1 item | 1.2 |
| Onions | 47 | 1 cup | 1.2 |
| Potato | 31 | 1.5 cups | 1.7 |
| Corn | 25 | 1.5 cups | 1.6 |

Figure 1, cont.

Fruit

| | | | |
|---|---|---|---|
| Strawberries | 212 | 1.5 cups | 7.0 |
| Pomegranate Juice | 193 | 4 oz | 6.4 |
| Plums | 158 | 3 items | 6.5 |
| Raspberries | 145 | 1.5 cups | 6.0 |
| Blueberries | 130 | 1.5 cups | 6.4 |
| Orange | 109 | 1 item | 3.6 |
| Grapefruit | 102 | 1.5 cups | 5.0 |
| Cantaloupe | 100 | 2 cups | 4.1 |
| Kiwi | 97 | 2 items | 4.0 |
| Watermelon | 91 | 2.5 cups | 3.7 |
| Orange Juice | 86 | 8 oz | 3.5 |
| Apple | 76 | 1 item | 2.5 |
| Peach | 73 | 2 items | 2.4 |
| Cherries | 68 | 1.5 cups | 3.3 |
| Pineapple | 64 | 1.5 cups | 2.6 |
| Apricots | 64 | 4 items | 2.1 |
| Mango | 51 | 1 item | 2.5 |
| Prunes | 47 | ¼ cup | 1.9 |
| Pears | 46 | 1 item | 1.9 |
| Honeydew Melon | 45 | 2 cups | 2.2 |
| Avocado | 38 | half | 2.6 |
| Grapes | 31 | 1.5 cups | 1.3 |
| Banana | 30 | 1 item | 1.2 |
| Figs | 25 | ¼ cup | 1.2 |
| Dates | 19 | ¼ cup | 0.9 |
| Raisins | 16 | ¼ cup | 0.7 |

Nuts

| | | | |
|---|---|---|---|
| Brazil Nuts | 116 | ¼ cup | 6.9 |
| Sunflower Seeds | 46 | ¼ cup | 2.5 |
| Flax Seeds | 44 | 2 T | 1.8 |
| Sesame Seeds | 41 | ¼ cup | 2.4 |
| Pecans | 34 | ¼ cup | 1.8 |
| Pumpkin Seeds | 36 | ¼ cup | 1.9 |
| Tahini Butter | 32 | 2 T | 1.7 |
| Walnuts | 29 | ¼ cup | 1.6 |
| Pistachios | 29 | ¼ cup | 1.6 |
| Almonds | 25 | ¼ cup | 1.5 |
| Peanuts | 19 | ¼ cup | 1.1 |
| Peanut Butter | 18 | 2 T | 1.0 |
| Cashews | 15 | ¼ cup | 0.8 |
| Cashew Butter | 13 | 2 T | 0.7 |
| Pine Nuts | 10 | ¼ cup | 0.6 |
| Macadamias | 10 | ¼ cup | 0.6 |

Figure 1, cont.

Beans

| | | | |
|---|---|---|---|
| Tofu | 86 | 4 oz | 2.8 |
| Lentils | 68 | 1 cup | 4.0 |
| Black Beans | 58 | 1 cup | 3.4 |
| Edamame | 58 | 1 cup | 3.7 |
| Adzuki Beans | 56 | 1 cup | 3.6 |
| Kidney Beans | 56 | 1 cup | 3.3 |
| Soybeans | 48 | 1 cup | 3.1 |
| Chick Peas | 48 | 1 cup | 3.1 |
| Soy Burgers | 45 | 1 item | 2.2 |
| Soy Milk | 33 | 8 oz | 1.6 |
| Soy Cheese | 27 | ½ cup | 1.5 |

Grains

| | | | |
|---|---|---|---|
| Oats, cooked | 53 | 1 cup | 2.6 |
| Brown Rice, cooked | 41 | 1 cup | 2.4 |
| Sprouted Grain Bread | 39 | 1 slice | 5.5 |
| Barley, cooked | 32 | 1 cup | 1.7 |
| Whole Wheat Bread | 25 | 1 slice | .8 |
| Quinoa, cooked | 21 | 1 cup | 1.2 |
| Whole Wheat Pasta, cooked | 19 | 2 cups | 1.3 |
| White Pasta, cooked | 18 | 2 cups | 1.3 |
| White Bread | 18 | 1 slice | 0.9 |
| Bagel, whole grain | 18 | 1 item | 1.0 |
| White Rice, cooked | 12 | 1 cup | 0.7 |

Fish

| | | | |
|---|---|---|---|
| Yellow fin Tuna | 46 | 3 oz | 1.9 |
| Flounder/Sole | 41 | 3 oz | 1.7 |
| Salmon | 39 | 3 oz | 1.9 |
| Swordfish | 38 | 3 oz | 1.9 |
| Shrimp | 38 | 3 oz | 1.3 |
| Canned Tuna, in water | 36 | 3 oz | 1.5 |
| Cod | 31 | 3 oz | 1.0 |

Figure 1, cont.

Dairy

| | | | |
|---|---|---|---|
| Skim Milk | 36 | 8 oz | 1.4 |
| Plain Yogurt, low fat | 26 | 1 cup | 1.4 |
| Feta Cheese | 23 | 2 oz | 1.2 |
| Whole Milk | 20 | 8 oz | 1.0 |
| Cottage Cheese, low fat | 18 | 1 cup | 1.0 |
| Fruit Yogurt, low fat | 14 | 1 cup | 0.9 |
| Cheddar Cheese | 11 | 2 oz | 0.7 |
| American Cheese | 10 | 2 oz | 0.6 |
| Vanilla Ice Cream | 9 | 1 cup | 0.6 |
| Vanilla Frozen Yogurt | 9 | 1 cup | 0.6 |
| Cream Cheese | 4 | 4 tablespoons | 0.2 |

Meat

| | | | |
|---|---|---|---|
| Deli Turkey Breast | 33 | 3 oz (3 slices) | 1.4 |
| Eggs | 28 | 2 items | 1.4 |
| Chicken Breast | 27 | 3 oz | 1.3 |
| London Broil | 26 | 3 oz | 1.4 |
| Pork Loin | 23 | 3 oz | 1.4 |
| Ground Beef | 20 | 3 oz | 1.2 |
| Bologna | 13 | 3 oz (3 slices) | 0.8 |
| Hot Dog, beef | 8 | 1 item | 0.4 |

Refined/Processed Foods

| | | | |
|---|---|---|---|
| Milk Chocolate Bar | 21 | 1 bar (43g) | 1.2 |
| Pizza | 17 | 2 slices | 1.2 |
| Popcorn | 16 | 4 cups | 0.8 |
| McDonalds Cheeseburger | 15 | 1 item | 1.0 |
| Pretzels | 13 | 10 items | 0.8 |
| Potato Chips | 11 | 1 oz (10 items) | 0.6 |
| Saltine Crackers | 11 | 5 items | 0.4 |
| Granola Bars, Chocolate Chip | 11 | 1 item | 0.4 |
| McDonalds French Fries | 7 | medium bag | 0.5 |
| Sugar Cookies | 5 | 2 items | 0.3 |
| Corn Oil | 3 | 1 Tablespoon | 0.1 |
| Olive Oil | 2 | 1 Tablespoon | 0.1 |
| Honey | 1 | 1 Tablespoon | 0.0 |
| Cola | 0.5 | 8 oz | 0.0 |

METHODS FOR DEVELOPING AND CONDUCTING A NUTRITIONAL TREATMENT PROGRAM

CROSS-REFERENCE TO RELATED APPLICATIONS

This application is a continuation-in-part application of U.S. Ser. No. 11/906,239, filed Oct. 1, 2007, which claims priority under 35 U.S.C. §119(e) to U.S. provisional application 60/848,499, filed Sep. 29, 2006.

TECHNICAL FIELD

The present invention relates to methods for developing and conducting a nutritional treatment program. In one embodiment, the present invention relates to methods for developing and conducting a nutritional treatment program to promote weight loss, or to treat or prevent other disease states, such as diabetes, heart disease, hypertension, etc. For example, such methods are employed to develop a diet program, and more particularly to methods for developing a program for both dieting and maintaining good nutrition both before and after losing weight. In another embodiment, the present invention relates to personalized nutritional treatment programs that are computer implemented and dynamic based on a subject's changing health condition.

BACKGROUND OF THE INVENTION

Numerous nutritional programs have been offered to the public over the years. Most such programs designed for losing weight rely on limiting food intake based on one or more criteria, such as calories, carbohydrates, etc. For example, the Atkins diet (Atkins Nutritionals, Inc.) focuses on severely limiting carbohydrate intake. However, such a restricted diet can have a variety of dangerous side effects, such as an increased risk of heart disease due to a high fat intake.

Another diet program, the South Beach Diet™ (www.southbeachdiet.com) is based on a characterization of carbohydrates, fats and proteins as being "good" or bad". However, while being more balanced than a program based on a single criteria (e.g., calories), it is somewhat restrictive and does not have a good compliance rate.

The Zone Diet (Zone Labs, Inc., Danvers, Mass.), in comparison, is based on characterizing food in terms of protein, fat and carbohydrate content, and selecting food on the basis of the relative amounts of these three substances. While being more balanced and having a satisfactory compliance rate, it is still somewhat difficult to follow, since it relies heavily on the dieter being capable of estimating what foods to select and how to incorporate the diet into daily and long term programs.

Other types of diet programs rely on the use of appetite suppressants, which are usually stimulants that are not well tolerated by individuals with high blood pressure or other medical conditions that are often associated with obesity. Still other diet programs are based on strict dietary intake by supplying prepackaged food, or are based on behavior modification in a support group setting.

More recently, nutritional programs have been described based on "nutrient density", which is a term that is unfortunately used inconsistently in the industry, and may be based on calories/nutrients, nutrients/calories, or nutrients/nutrients (Am. J. Clin. Nutr. 82:721-732 (2005). Such a program may be utilized in the online Nutripoints diet program which characterizes foods in six food groups and scores foods based on their "nutritional value" (www.nutripoints.com, Nutripoints, Inc., Carlsbad, Calif.).

In addition to the aforementioned nutritional programs designed to promote and maintain weight loss, the same principles of nutritional control can be applied to other disease states, such as diabetes, heart disease and hypertension. For example, nutrition programs designed to assist individuals suffering from diabetes are well known and often involve a combination of controlling the uptake of specific nutrients, as well as sugar. In another example, nutritional programs to prevent cancer are known to focus on increasing ingestion of anti-oxidants and other vitamins, such as vitamins C and E.

Accordingly, there is an urgent need in the art for a program and associated methodology to permit one to both lose weight, obtain a lifetime of good nutrition, and to alter eating habits in order to maintain weight loss and good health. There is also a need for programs that are designed to prevent and treat other conditions and disease states based on the principals normally associated with nutrition programs for weight loss.

SUMMARY OF THE INVENTION

The present invention relates, in part, to a method for administering a daily nutritional program to a subject to address a health condition comprising the steps of: a) establishing an aggregate nutrient density index (ANDI) score for foods to be ingested on the program, wherein the ANDI score is relative to an ideal reference food that contains selected nutrients having high nutrient per calorie ratios; b) establishing a menu aggregate nutrient density index (MANDI) value for the foods, wherein the MANDI value is established by multiplying the ANDI by a number equal to or directly proportional to the number of calories per serving of the food to be consumed on the program; and c) directing the subject to ingest the food to achieve a preestablished daily MANDI score during the program.

The program may also employ a preestablished daily MANDI score is increased over time on the program, and may also be divided up into two or more phases, each phase consisting of two or more days, and each phase having a different preestablished daily MANDI.

The selected nutrients can be selected to address any health condition, but in one embodiment, the selected nutrients include at least one vitamin, at least one mineral, fiber, carotenoids, glucosinolate and anti-oxidants.

The health conditions to be addressed by the nutrition program may include, for example, obesity, diabetes, heart disease and hypertension, as well as other disease states and health conditions.

In another embodiment, the invention relates to a method for creating a daily nutritional program to a subject to address a health condition comprising the steps of: a) establishing an aggregate nutrient density index (ANDI) score for foods to be ingested on the program, wherein the ANDI score is relative to an ideal reference food that contains selected nutrients having high nutrient per calorie ratios, and wherein the ANDI score is established by using a computer or by referring to a list of ANDI scores stored in computer memory; b) establishing a menu aggregate nutrient density index (MANDI) value for the foods, wherein the MANDI value is established by multiplying the ANDI by a number equal to or directly proportional to the number of calories per serving of the food to be consumed on the program; and c) designing a daily menu plan based on a minimum daily MANDI score for each day of the program.

In yet another embodiment of the present invention ANDI may be weighted by: a) identifying an undesirable nutrient that is associated with the health condition; b) determining an undesirable nutrient value for each food in the ANDI; and c) weighting the ANDI scores by dividing by the nutrient value. Representative undesirable nutrients include, for example, salt, sugar and saturated fat.

In an embodiment of the present invention involving personalization, the invention pertains to a method for creating a dynamic personalized nutritional treatment program for a subject to address a health condition, wherein the program comprises the steps of: a) providing an nutritional density index (NDI) comprised of NDI scores for a plurality of foods, wherein the NDI is stored on a computer; b) entering at least one health parameter reflective of the subject's health condition; c) selecting at least one food item from foods listed in the NDI; and d) applying a mathematical algorithm using a computer to the NDI to generate an output for the subject, wherein the output comprises a recommended intake value of the food item based on the health parameter.

As described above for ANDI, the NDI may also be weighted by dividing the NDI scores for each food in the NDI by an undesirable nutrient value.

The health parameter for use in the personalized embodiment may be, for example, glucose, low density lipoprotein (LDL) cholesterol, hemoglobin A1c (HbA1c), body mass index (BMI) and blood pressure.

Other aspects of the invention are described throughout the specification.

BRIEF DESCRIPTION OF THE FIGURES

FIG. 1 depicts the ANDI and MANDI values for commonly eaten foods.

DETAILED DESCRIPTION OF THE INVENTION

The present invention relates to methods for developing and conducting a "nutritional treatment program", i.e., a program for promoting good nutrition for the purpose of preventing or treating a health condition or disease state, as well as for the purpose of maintaining a healthy condition. In one embodiment, the present invention relates to methods for developing and conducting a nutritional program to promote weight loss. Such methods generally relate to a diet program, and more particularly to methods for dieting and maintaining good nutrition both before and after losing weight.

In another embodiment, the present invention relates to personalized nutritional treatment programs that are computer implemented and dynamic based on a subject's changing health condition.

The nutritional treatment program of the present invention is principally based on characterizing food in terms of both their "aggregate nutrient density index", or "ANDI", and their "menu aggregate nutrient density index", or "MANDI". In addition, the program may be executed in one or more "phases" as more fully described elsewhere herein.

Overview of an Exemplary Embodiment

The "ANDI" Nutrient Score in this embodiment is a rating system that scores foods on a scale of 0-1000. It is based on how many nutrients are in an equal caloric amount of each food. Using a specific calorie amount instead of weight or serving size is a more accurate way of obtaining a pure "nutrient per calorie" score. The most nutrient dense foods (green leafy vegetables such as kale, watercress and mustard greens) score 1000; all other foods are then scored relative to them. The use of a scale of 0-1000 gives a true picture of the amazing nutrient density of vegetables compared to the foods that typically make up the Standard American Diet (SAD). Most SAD foods score less than 25.

The "MANDI" Point System uses "ANDI" Nutrient Scores to assign point values to specific serving sizes of individual foods and recipes. It allows rating of daily menus. Using a simple equation, the ANDI, and the calories per serving, "MANDI" is calculated using a scoring system based on 100. A daily intake of 100 points of MANDI represents the ideal diet. FIG. 1 lists the point values for a variety of commonly eaten foods based on an ANDI to promote weight loss. If the serving size shown in FIG. 1 is different than the desired serving size, a different MANDI nutrient point value can easily be calculated.

The program is based on maximizing MANDI points, and in one embodiment, can be designed to be carried out in four phases with the nutrient density of the foods consumed increasing gradually from adequate to superior.

Individual foods and recipes are assigned points so one can learn which foods are the most nutrient dense in order to devise menus to be high in nutrients. The goal for Phase 1 is to reach a total score of 60 for each day. Menus can be constructed to design meals that give an average score of 60 per day over the course of a week. Since greens are highest in nutrient density, the secret to getting a high score is to include as many greens in the menu as possible. Generally in Phase 1, menus will contain more than triple the level of nutrients consumed by most Americans. The four phases can be designed to gradually increase to a diet that earns 70, 80, 90 or 100 nutrient points. The scores are designed to make 100 the ideal score. It is generally easier for a male eating more calories to reach this total and harder for a women consuming less calories, but overeating to increase the point value defeats the purpose of the program.

The following table exemplifies a program designed for weight loss to be accomplished in four phases, with optional additional limitations on food intake in each of the four phases based on other criteria in addition to MANDI.

TABLE 1

| | Overview of the Four Phases | | | |
| --- | --- | --- | --- | --- |
| | Phase 1 | Phase 2 | Phase 3 | Phase 4 |
| MANDI | 60 | 75 | 90 | 100+ |
| Animal Products | 8 servings/week | 5 servings/week | 3 servings/week | 2 servings/week |
| Sodium* | 1600 mg/day | 1200 mg/day | 1000 mg/day | 900 mg/day |
| Grains** and Starchy Vegetable*** | 14/week | 12/week | 10/week | 7/week |
| Fats/Oils | 1 Tbsp of olive oil or replaceable | 1 Tbsp of olive oil or replaceable | 1 Tbsp of olive oil twice weekly | Minimal |

TABLE 1-continued

Overview of the Four Phases

|  | Phase 1 | Phase 2 | Phase 3 | Phase 4 |
|---|---|---|---|---|
|  | substitute**** per day | substitute**** per day |  |  |
| Beverage | Water, fresh squeezed juice, herbal teas If desired 1 cup coffee/tea | Water, fresh squeezed juice, herbal tea, if desired, 1 cup coffee/tea | Water, fresh squeezed juice, herbal tea | Water, fresh squeezed fruit and vegetable juices |
| Cooking Methods | Reducing salt and substituting other seasonings ---------- Cooking with Minimal Oil ---------- Creating fruit smoothies | Soups and Stews | Using nuts, seeds, avocados and tahini in place of oil ---------- Water sautéing ---------- Sweetening nutrient dense desserts with dates and dried fruit | Juicing and vegetable smoothies (blended salads) |
| Concepts | Reducing sodium Increasing fruit and green vegetables | Adding more beans and nuts Reducing animal products Continuing to reduce sodium Adding more green vegetables | Eliminating oil Eliminating caffeine Continuing to reduce animal products Continuing to reduce sodium Adding more green vegetables and fruit | Maximizing nutrient density and absorption |

*The amount of sodium allotted includes that which is naturally occurring in foods (appox. 700 mg) plus what is added.
**Grains include: bread, tortillas, crackers, cooked/dry cereals, pasta, rice
***Starchy Vegetables include: corn, white potatoes, sweet potatoes, squash, carrots, parsnips
****Substitutes include: non-dairy spreads without trans-fats and hydrogenated oil such as: Earth Balance, Smart Balance, Spectrum, Calculating ANDI The term "ANDI" as used herein means a nutrient score that is relative to an ideal reference food that contains selected nutrients having high nutrient per calorie ratios. By being "high", it is intended that the ideal reference food is recognized to be in the top 25%, and preferably the top 10% of all foods that typically make up the "Standard American Diet" (SAD).

The ANDI for a particular food is preferably calculated by first selecting one or more nutrients (i.e., "selected nutrients") believed or known to be associated with a health condition or disease state, or a combination of such conditions/states. For example, a combination of nutrients that includes at least one vitamin, at least one mineral, fiber, carotenoids, glucosinolate and anti-oxidants, can be used as a starting point to design a program to promote both weight loss and prevent cancer. Then, the amount of each nutrient in a "standard quantity of calories", such as 1000, is calculated to determine the "nutrient quantity". Next, the nutrient quantity is divided by the recommended daily intake (RDI) for that nutrient (in the units normally used to express RDI for the nutrient, such as milligrams, mg, for Vitamin C) to determine the "% RDI" of that nutrient in the standard quantity of calories. Then the % RDIs for the selected nutrients are added together.

A "reference food" is also selected based on its high total "selected nutrients" values, and a "normalizing factor" is calculated based on this food's total % RDI of the selected nutrients. This normalizing factor is used to determine the ANDI for the selected food, which is relative to the reference food.

For example, if the reference food has a total % RDI of 25,000 and the reference food is assigned a top value of 1000, then the normalizing factor would be 1000/25,000, or 0.04. Thus, the nutritional "value" of all foods can be compared to this "reference food".

In summary, ANDI is calculated as follows:

Selected Nutrient(s) (SN) in a Selected Food/Set Number of Calories (C)=Nutrient Quantity (NQ)

Nutrient Quantity/RDI×100=% RDI

Total % RDIs for all Selected Nutrients in the Selected Food×Normalizing Factor (NF)=ANDI The selected nutrient or nutrients can be made or compiled from well known published literature which associates nutrients with a particular health condition or disease state. Medical personnel and individuals can therefore easily customize the selected nutrient list based on the desired effect of the nutritional program.

In addition, ANDI need not be calculated once a list of ANDI scores are established for a number of foods. Thereafter, ANDI can be estimated based on the similarity of a selected food to a food having a known ANDI score. Also, ANDI scores for combinations of foods, or "recipes" can be established based on the proportions of different foods in the recipe, or simply estimated based on the known ANDI scores of the principle foods in such recipes.

Representative Method of Calculating ANDI

In one embodiment of a method for promoting weight loss and good general health, ANDI is calculated based on 17 different nutrients. Nutrient Data for each food item is obtained for the amount of that food that would provide 1000 calories. Information is obtained, for example, using the "Nutritionist Pro" food data base (Nutritionist Pro Nutritional Analysis Software Versions 2.5, 3.1 (2005, 2006), Axxya Systems, Stafford Tex.). The following nutrients are included in the evaluation:

Vitamin C
Calcium
Iron

Vitamin E
Thiamin
Riboflavin
Niacin
Vitamin B12
Vitamin B6
Folate
Magnesium
Zinc
Selenium
Dietary Fiber (total)
Carotenoids:
  Beta Carotene, Alpha Carotene, Lutein & Zeaxanthin, Lycopene
Glucosinolate—compounds from cruciferous vegetables
ORAC score—Oxygen Radical Absorbance Capacity is a method of measuring the antioxidant or radical scavenging capacity of foods (Wu, X., et al., Journal of Agricultural and Food Chemistry 52:4026-4037 (2004))
Nutrient quantities were converted to a percentage of their "recommended daily intake, or "RDI". Since there is currently no RDI for Carotenoids, Glucosinolates, or ORAC score, the following goals were established based on available research and current understanding of the benefits of these factors:
  Carotenoids ("Dietary Reference Intakes for Vitamin C, Vitamin E, Selenium, and Carotenoids", Food and Nutrition Board. Institute of Medicine. National Academy Press, Washington D.C., Pp. 343-344 (2000)
    Beta Carotene 6.0 mg
    Alpha Carotene 1.5 mg
    Lutein & Zeaxanthin 4.2 mg
    Lycopene 6.5 mg
  Glucosinolate (Higdon, Jane. "Isothiocyanates", The Linus Pauling Institute. Micronutrient Research Center (2005), www.oregonstate.edu/infocenter/phytochemicals/isothio)
    Ten servings per week of cruciferous vegetables was considered to be optimal. It was determined that on average, 10 servings per week would translate to a daily goal of 35 mg.
  ORAC (McBride, Judy, Agricultural Research, 47(2):15-17 (1999)
    Evidence suggests that daily intake be increased to between 3000-5000 ORAC units to have significant impact on plasma and tissue antioxidant capacity. A goal of 5000 ORAC units was chosen.

The % RDI for each nutrient is added together to give a total for each food item. (The ORAC score was given a weight of 2 due to the importance of antioxidant nutrients)

Since the total for kale (the reference food in this example) is at or near the top of all commonly consumed foods, that number is multiplied by 0.02472 (the normalizing factor in this example) to make kale's total score=1000. Each food's total nutrient value is then multiplied by this same factor of 0.02472. This factor is: 1000/total nutrient value of kale. So, all other foods then received their ANDI relative to kale being 1000.

Where possible, values for calories, sodium and all nutrients other than Glucosinolate and ORAC are obtained from the USDA Database for Standard Reference.

Calculating MANDI

MANDI is used to establish a daily intake goal based on MANDI. In the simplest embodiment, MANDI is calculated by multiplying ANDI by a number equal to or directly proportional to the calories per serving of food to be consumed. A daily MANDI goal can be established based on the MANDI of a model "daily food intake plan" based on known literature describing ideal daily menu plans for different health conditions.

In another embodiment, MANDI is calculated based on the assignment of a "calorie factor" (CF) that is directly proportional to the number of calories per serving in a selected food. For example, a low calorie food will be assigned a low calorie factor, and a high calorie food will be assigned a high calorie factor.

If the ANDI for a combination of foods, or a "recipe" is either calculated or estimated, the calorie factor can also be multiplied by any number between 1 and 2 to account for the fact that the ANDI score for the recipe may be falsely low due to the presence of unaccounted for ingredients in the recipe.

In another example, if ANDI is established by assigning "1000" as the ANDI score of the reference food, then MANDI can be calculated as follows:

$$ANDI/1000 \times \text{Calorie Factor} = MANDI$$

Representative Method for Calculating MANDI

In this example, the calorie factors used for food are half those of recipes as follows:

TABLE 2

| Calorie Range | Calorie Factor | |
|---|---|---|
| | Food Items | Recipes (×2) |
| 0-29 | 17 | 34 |
| 30-59 | 25 | 50 |
| 60-89 | 33 | 66 |
| 90-119 | 41 | 82 |
| 120-149 | 49 | 98 |
| 150-199 | 54 | 108 |
| 200-249 | 59 | 118 |
| 250-299 | 64 | 128 |
| 300 and up | 69 | 138 |

Using these calorie factors and the ANDI scores established using the Representative Method for Calculating ANDI above, MANDI values for a nutritional program to promote weight loss is calculated from: ANDI/1000×Calorie Factor=MANDI.

Weighted ANDI

As discussed above, the nutritional treatment program of the present invention is "customized" to a particular health goal or goals, such as weight loss, diabetes prevention, lowering of blood pressure, etc. Customization is achieved by choosing "selected nutrients" to calculate ANDI scores to compile an ANDI (i.e., an index consisting of a plurality of ANDI scores for different foods) that are considered nutritious in the context of the particular health goal to be achieved. Thus, the ANDI value is based on the relative density of good nutrients in a particular food, since the nutrients are selected based on their ability to promote good health.

Another way of customizing ANDI to a particular health goal is to start with ANDI values that are based on a plurality of selected nutrients reflective of general good health. In the representative method of calculating ANDI above, the selected basic nutrients consist of 17 nutrients that are generally considered to promote good health. Other examples of "selected good nutrients" include, for example, the 14 basic "nutrients of public health importance" (Drewnowski, A., Am. J. Clin. Nutr. 82: 721-732 (2005); as listed by the Food and Agriculture Organization (FAO) of the United Nations)). These are: protein, vitamin A, vitamin C, calcium, iron, zinc, folate, thiamine, riboflavin, vitamin B-12, vitamin D, vitamin E, niacin, vitamin K, vitamin B-6, fiber and potassium. Still other lists of "selected good nutrients" are well known in the literature. However, there is no universally accepted list of "selected good nutrients", although they almost always include at least 10 out of the 14 basic "nutrients of public health importance".

Starting with these general (as opposed to customized) ANDI values, the values can be tailored to a particular health goal or goals by weighting the value in terms of the presence of nutrients that are considered undesirable for a particular health condition. For example, excessive sugar is an undesirable component of foods to be eaten by a diabetic subject. Other examples are excessive saturated fat in a diet for a patient with coronary artery disease, or excessive sodium in a diet for a patient with hypertension. Thus, sugar, saturated fat and sodium may be considered to be "bad nutrients". Accordingly, a weighted ANDI is easily calculated by lowering the ANDI value in proportion to the amount of a particular bad nutrient present in the food. For example, if a carrot has an ANDI value of 288, but has far too much sugar to be consumed by a diabetic patient, the ANDI value may be weighted down to 200, which would put it in a category to be consumed in moderation by a diabetic patient.

More simply put,

Weighted ANDI=ANDI÷Bad Nutrient Content Factor

As with all "factors", they may be either absolute (e.g., directly proportional to the amount of sugar in a food) or scaled (e.g., assigned a value of 1 to 5 based on the absolute amount of sugar in the food falling within any of five different ranges).

Personalized Nutritional Program

The ANDI value, which may be either weighted or not, can also be used to develop a "personalized" dietary plan that is unique to a particular subject's dynamic health condition and/or dietary goals. Accordingly, in another embodiment of the present invention, the nutritional treatment program described above can be individually personalized based on a subject's unique health parameters at any given time, such as weight, body mass index (BMI), cholesterol level, glucose level, hemoglobin A1c (HbA1c) level, etc. In such an embodiment, ANDI values are scaled into categories on the basis of their availability to be included in the nutritional treatment program at any given time, i.e. there is a "sliding scale" depending on the health condition of the subject at any given time.

In this embodiment, health parameters are scaled into categories on the basis of value ranges and ranked from 0 (i.e., normal) to 4 (i.e., significantly abnormal).

TABLE 3

| Glucose | LDL Cholesterol | BMI | Systolic Blood Pressure |
|---|---|---|---|
| <100 (0) | <100 (0) | <24 (0) | <120 (0) |
| 100-120 (1) | 100-120 (1) | 25-28 (1) | 121-140 (1) |
| 121-140 (2) | 121-140 (2) | 29-32 (2) | 141-160 (2) |
| 141-160 (3) | 141-160 (3) | 33-36 (3) | 161-180 (3) |
| >160 (4) | >160 (4) | >36 (4) | >180 (4) |

Then, a sliding ANDI, or "SANDI", scale is established, which may be the same or different depending on the health condition, the health parameter and/or the "bad nutrient(s)" included in the weighted ANDI. For example, Table 4 depicts a SANDI scale that may be applicable to all health parameters listed in Table 3:

TABLE 4

| ANDI Score Range | Recommended Intake (Rank) |
|---|---|
| >100 | Unlimited (0-4) |
| 80-100 | Limited 2/day (0-1) |
|  | Limited 1/day (2-4) |
| 60-80 | Limited 1/day (0-4) |
| 40-60 | Limited 1/day (0-2) |
|  | Rarely 1/wk (3-4) |
| 20-40 | Rarely 2/wk (0-2) |
|  | Never (3-4) |
| <20 | Never (0-4) |

According to this sliding scale method, ANDI can be divided into any number of categories, and the Recommended Intake of a particular food can be determined by reference to the sliding scale of permissible intake amounts, depending on the health parameter ranking. For example, a person with a glucose level of 130 falls into category 2 as shown in Table 3. This corresponds to a Recommended Intake amount of 1 per day for foods with an ANDI score of 40-100. As the subject's glucose level decreases to 110, which falls into category 1, their Recommended Intake increases or "slides" to 2 per day for foods with an ANDI score of 80-100. Conversely, if the subject's glucose level increases to 150 which falls in the third category, their recommended intake would be curtailed, for example, to eliminate foods with an ANDI score below 40.

In addition, the recommended intake values in the sliding scale may also change over time as the subject's health parameters change.

In addition to using ANDI values as described herein, the personalized nutritional program described herein, which incorporates a recommended intake scale that is dynamic (i.e., it "slides") on the basis of a subject's health parameter or parameters at any given time can also be based on any known or calculated, weighted or unweighted, nutritional density index, one example of which is the naturally nutrient rich (NNR) score index, which is described in A. Drewnowski, supra, along with other indexes. Collectively, such indexes that rank foods on the basis of their overall nutritional value are referred to as an "NDI". Such NDIs can be based on any combination of calorie-to-nutrient ratios, nutrient-to-calorie ratios, or nutrient-to-nutrient ratios.

Creating a Nutrition Program

A nutrition program is created using the ANDI and MANDI values described above to address any health condition. "Addressing a health condition" means that the nutrition program is designed to treat or prevent a medical condition or disease state, such as excess weight, diabetes, heart disease, or hypertension, or the "health problem" may simply mean that the subject has a problem maintaining good nutrition or a weight goal.

It is generally convenient to use a computer (which includes a calculator) with memory to establish and store ANDI values. This allows easier customization of ANDI values for various health conditions, and permits ANDI values for selected foods to be estimated based on a comparison with preestablished ANDI values for similar foods.

After establishing ANDI, MANDI can be easily established based on the number of calories per serving of food to be consumed on the program. From there, once a minimum MANDI value for individual days of the nutrition program is established, daily menu plans can be generated based on the aggregate MANDI values of all the food on the daily menu.

Administering the Nutrition Program

Once the nutrition program has been created, which may or may not include preestablished daily menus for each day on the program, the individual foods and/or recipes that are necessary to achieve the daily MANDI goal are directed to be ingested by or administered to the subject on the nutritional program.

Computerizing the Nutrition Program

As described above, the calculations that may or may not be necessary for any particular nutritional treatment program include:
 ANDI
 MANDI
 Weighted NDI In addition, the scaling of the NDI and the health parameters, if utilized in a personalized nutritional treatment program, is necessarily preestablished or "calculated" before implementing the nutritional treatment program, although the scaling may be altered from time to time during the program.

Accordingly, the nutritional treatment program is implemented by storing the NDI in computer memory, then designing the dietary plan based on reference to the stored NDI, and alternatively also the stored scaled NDI and stored scaled health parameters.

In one embodiment, the NDI (and alternatively also any other calculated parameter) is stored on a personal computer, a personal digital assistant (PDA) device (which is also a type of computer), or it is stored on a server at a remote location which is accessible over the internet (wireless, dial-up, etc.) by a personal computer or personal digital assistant (PDA) device. The NDI may or may not be "read only", such that the end user or medical health care professional can edit the NDI to adapt it to a particular situation or for a particular subject.

In "read only" format, the NDI may be updated on demand by access to an updated NDI which is made available over the internet from a remote location. Alternatively, the NDI may be updated using any computer readable medium such as a computer disk, thumb drive or computer chip that can be loaded and/or interchanged into or onto a personal computer or PDA.

To implement a dynamic personalized nutritional treatment program, the personalized computer, PDA or computer storage device at a remote location must be able to receive dynamic personal input from a subject (either directly or indirectly as is the case when the nutritional treatment program is being implemented and managed by a health care professional), and the output such as the recommended intake of foods in the nutritional treatment program must in some way be reflective of this input.

In an entirely internet-based application of the personalized nutritional treatment program, a subject accesses a centralized computer at a remote location over the internet, and inputs or chooses from a list their health condition (e.g., overweight, diabetes, hypertension). Alternatively, using a controlled access system requiring a user name and password, the centralized computer may default to a previously established health condition. Then, the present value of a health parameter (e.g., weight, BMI, glucose level, HbA1c level) is entered. An optional additional input may be the food that the subject wants to establish a recommended intake for. In this instance, the output could be the recommended intake for that particular food at that time, such as one serving per day. If the subject had already had a serving of that food earlier in the day, they would be discouraged from eating more of that particular food. If they had not already had a serving of that food, they would be discouraged from including this in their diet at all.

An additional component of the computerized system of the present invention is that the output to the subject (or other user) may also include a time frame within which they should repeat the determination and input of their health parameter(s). For example, if the input requested by the system required the time to be entered along with a glucose level, in addition to the recommended intake of a food item as output, the output may also include a recommendation to repeat the glucose test in 8 hours. Other medical alerts, such as "Call your Doctor", "Call 911", can also easily be incorporated into this system.

An extension of this type of dynamic personalized input/output that is not food-specific can also include the output of a daily menu plan chosen from stored meals that are appropriate for the subject based on the value of the health parameter they input at any given time. Such menu plans and all of the aforementioned input and output can conveniently be stored on the centralized computer, a personalized computer or a PDA, or any combination thereof.

EXAMPLE

In one example of the method of the present invention, the ANDI depicted in FIG. 1 is used. This ANDI is stored on a server at a centralized location and modified from time to time by the server administrator. Optionally, serving sizes for each food item listed in the ANDI are also stored on the server. The ANDI scores stored on the server are also scaled into six different categories from highest to lowest, the highest category being reflective of the most desirable foods listed in the ANDI.

A subject (or other user such as a health care professional) operating a PDA accesses the server via an internet service provider over the internet, which recognizes that the subject has diabetes on the basis of a user name and password or PDA identity unique to the subject.

The subject, having just measured their glucose level enters it into the PDA which transmits it to the server. The glucose level is associated with a preestablished rank stored on the server associated with a given glucose value range, with the lowest rank being reflective of a normal glucose level and the highest rank reflective of a severely abnormal glucose level.

The subject also identifies one or more foods listed in the ANDI that they would like to eat.

A mathematical algorithm is applied by the server, which determines a recommended intake for each identified food item and transmits it back to the subject, with optional information about serving size.

As the subject's glucose level fluctuates with time, the recommended intake for food items in ANDI is also adjusted accordingly.

The examples set forth above are provided to give those of ordinary skill in the art with a complete disclosure and description of how to make and use the preferred embodiments of the present invention, and are not intended to limit the scope of what the inventors regard as their invention. Modifications of the above-described modes (for carrying out the invention that are obvious to persons of skill in the art) are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A computer implemented method of administering a daily nutritional program to a subject for addressing a health condition of the subject, wherein the computer has memory, the method comprising the steps of:
   a. establishing an aggregate nutrient density index (ANDI) score for foods to be ingested on the program, wherein the ANDI score is calculated from a ratio of nutrients per calorie and is proportional to an ideal reference food that contains nutrients at a greater than a predetermined threshold value nutrient per calorie ratio, wherein the nutrients are selected from the group consisting of vitamins, minerals, fiber, carotenoids, glucosinolate and anti-oxidants;
   b. storing the ANDI score in the computer memory;
   c. using the computer to calculate a menu aggregate nutrient density index (MANDI) value for the foods by multiplying the ANDI score by a number equal to or directly proportional to the calories per serving of the food to be consumed by the subject on the program;
   d. storing the MANDI value in the computer memory;
   e. generating a daily menu plan on the computer based on a minimum daily MANDI score for each day of the program; and
   f. directing the subject to eat the foods according to the menu plan.

2. The method according to claim 1, further comprising the steps of:
   a. identifying an undesirable nutrient that is associated with the health condition;
   b. determining an undesirable nutrient value for each food having an ANDI score; and
   c. weighting the ANDI scores by dividing by the nutrient value.

* * * * *